United States Patent
Harding

(10) Patent No.: US 6,470,067 B1
(45) Date of Patent: Oct. 22, 2002

(54) COMPUTED TOMOGRAPHY APPARATUS FOR DETERMINING THE PULSE MOMENTUM TRANSFER SPECTRUM IN AN EXAMINATION ZONE

(75) Inventor: Geoffrey Harding, Hamburg (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 09/795,019

(22) Filed: Feb. 28, 2001

(30) Foreign Application Priority Data

Feb. 28, 2000 (DE) .......................... 100 09 285

(51) Int. Cl.[7] .............................................. G21K 1/10
(52) U.S. Cl. .............................................. 378/19; 378/6
(58) Field of Search .......................... 378/6, 7, 19, 154, 378/207

(56) References Cited

U.S. PATENT DOCUMENTS 4,995,107 A * 2/1991 Klingenbeck ................ 378/19
6,363,136 B1 * 3/2002 Flisikowski et al. ........ 378/147

* cited by examiner

*Primary Examiner*—David P. Porta
(74) *Attorney, Agent, or Firm*—John Vodopia

(57) ABSTRACT

A computed tomography apparatus includes a scanning unit which is rotatable relative to an examination zone, about an axis of rotation extending through the examination zone, a radiation source for generating a radiation beam, a diaphragm arrangement which is arranged between the radiation source and the examination zone in order to form a fan beam traversing the examination zone from the radiation beam, and a two-dimensional detector arrangement including a plurality of detector elements and a part of the measuring surface of which detects primary radiation from the fan beam whereas another part of its measuring surface detects scattered radiation produced in the examination zone. Perfect acquisition of the momentum transfer spectrum is achieved in that a collimator arrangement with a plurality of lamellas is arranged between the examination zone and the detector arrangement. The lamellas preferably are situated in planes that intersect each other at the focus of the radiation source and subdivide the fan beam into a number of segments so that the detector elements present in a column extending parallel to the axis of rotation are struck by primary radiation or scattered radiation from the same segment.

6 Claims, 2 Drawing Sheets

COMPUTED TOMOGRAPHY APPARATUS FOR DETERMINING THE PULSE MOMENTUM TRANSFER SPECTRUM IN AN EXAMINATION ZONE

FIELD OF THE INVENTION

The invention relates to a computed tomography apparatus which includes a scanning unit which is rotatable relative to an examination zone, about an axis of rotation extending through the examination zone, and includes a radiation source for generating a radiation beam, a diaphragm arrangement which is arranged between the radiation source and the examination zone in order to form a fan beam traversing the examination zone from the radiation beam, and a two-dimensional detector arrangement which includes a plurality of detector elements and a part of the measuring surface of which detects primary radiation from the fan beam whereas another part of its measuring surface detects scattered radiation produced in the examination zone.

BACKGROUND INFORMATION

Detector elements that are not directly exposed to the primary radiation are struck by scattered radiation that arises along the relevant primary beam throughout the object to be examined. The momentum transfer, being proportional to the product of the energy of the scattered quanta and the sine of half the scatter angle, can then be reconstructed by means of an iterative algebraic reconstruction technique (ART) which is described in detail in the cited D1. For each voxel in the examination zone which is traversed by a primary beam the reconstruction results in a momentum transfer spectrum (the momentum transfer spectrum represents the intensity of the scattered radiation as a function of the momentum transfer) that is characteristic of the matter in the relevant voxel and hence provides information as regards the physical composition.

A drawback of such a method is addressed already in said D1 and consists in the comparatively long measuring time required for the acquisition of all measuring data necessary for the reconstruction. In the cited D1 it is indicated that this measuring time can be reduced by means of a computed tomography apparatus, for example an apparatus having a fan beam geometry, be it that the measuring data is then more strongly corrupted by undesirable scattered radiation. The method which is known from WO 99/45843 has this drawback. Each detector element can then receive scattered radiation from the entire scatter fan beam, that is, also scattered radiation that is scattered at a comparatively large scatter angle (so mainly Compton scattered radiation) and does not offer any information as regards the physical composition of the examination zone. Moreover, there is no reconstruction method enabling the reconstruction of the scatter density in the examination zone in such circumstances.

OBJECTS AND SUMMARY OF THE INVENTION

Therefore, it is an object of the present invention to construct a computed tomography apparatus in such a manner that it offers short acquisition times on the one hand and a perfect reconstruction of the momentum transfer spectrum in the examination zone on the other hand. On the basis of a computed tomography apparatus of the kind set forth this object is achieved according to the invention in that between the examination zone and the detector arrangement there is provided a collimator arrangement which includes a plurality of lamellas which are situated in planes that subdivide the fan beam into a number of segments so that the detector elements that are situated in a column extending parallel to the axis of rotation are struck by primary radiation or scattered radiation from the same segment. The collimator arrangement according to the invention has a dual function: It prevents scattered radiation that has been scattered at a large scatter angle (so mainly Compton scattered radiation) from being incident on the detector elements. It subdivides the fan beam into a number of segments which are to be considered approximately as a "pencil beam", so that the momentum transfer spectra for the various voxels in the examination zone can be reconstructed by means of the method which is known from the cited D1.

In principle there are several possibilities for arranging the lamellas of the collimator arrangement that extend parallel to the axis of rotation or perpendicularly to the radiation beam.

One embodiment of the present invention enables the use of a computed tomography apparatus on the one hand for the determination of the momentum transfer spectra of the scattered radiation and on the other hand for the acquisition of the attenuation of the X-rays with an even further reduced acquisition time (cone beam CT) while using few additional means. In another embodiment of the present invention the necessary change-over takes place from a fan beam to a cone beam. Another embodiment deals with the processing of the various measuring data acquired in the various modes of operation.

BRIEF DESCRIPTION OF THE DRAWINGS

The invention will be described in detail hereinafter with reference to the drawings. Therein.

DETAILED DESCRIPTION OF THE PREFERRED EMBODIMENTS

Figure 1:
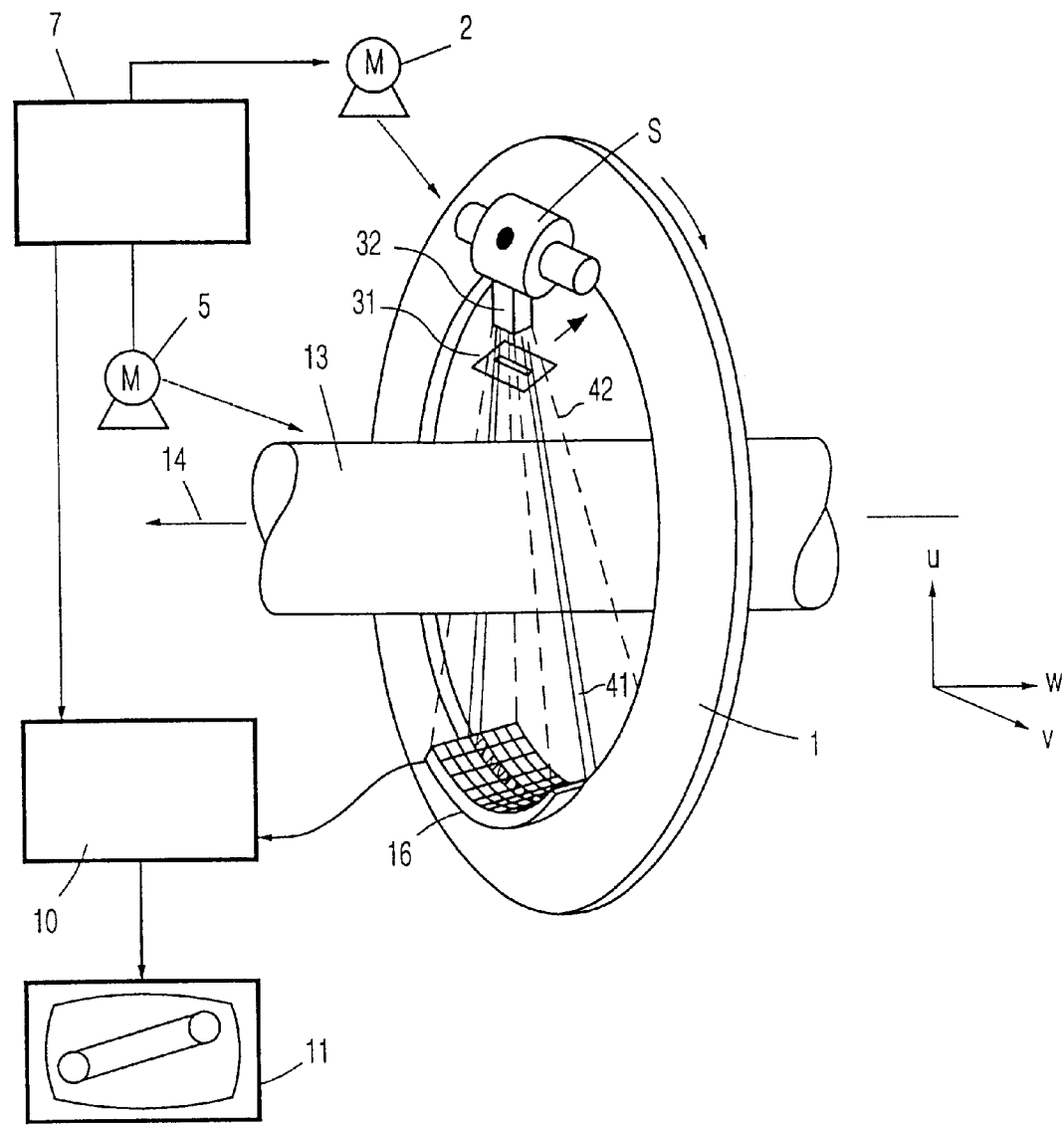
FIG. 1 shows diagrammatically a computed tomography apparatus according to the invention.

The computed tomography apparatus shown in FIG. 1 if includes a gantry 1 which is capable of rotation about an axis of rotation 14. To this end, the gantry 1 is driven by a motor 2. A radiation source S, for example an X-ray source, is mounted on the gantry 1. The radiation beam used for the examination is determined by a first diaphragm arrangement 31 and/or a second diaphragm arrangement 32. When the first diaphragm arrangement 31 is active, the fan beam shown in solid lines is obtained; this beam extends perpendicularly to the axis of rotation 14 and has small dimensions in that direction (for example, 1 mm). However, if only the second diaphragm arrangement 32 is active in the beam path, the cone beam 42 shown in dashed lines is obtained; in a plane perpendicular to the axis of rotation 14 this cone beam has the same shape as the fan beam 41, but its dimensions in the direction of the axis of rotation 14 are significantly larger.

The beam 41, or 42, penetrates a cylindrical examination zone 13 in which, for example, a patient on a patient table (both not shown) or a technical object may be present. After having traversed the examination zone 13, the beam 41, or 42, is incident on a two-dimensional detector arrangement 16 which is mounted on the gantry 1 and includes a plurality of detector elements which are arranged in the form of a matrix. The detector elements are arranged in rows and columns. The detector columns extend parallel to the axis of rotation and the detector rows may be situated in planes perpendicular to the axis of rotation, for example on an arc of a circle around the radiation source S. The detector rows usually contain a number of detector elements (for example, 1000) that is significantly larger than the number of detector elements present in the detector columns (for example, 16).

The beams 41 and 42, the examination zone 13 and the detector 16 are adapted to one another. The dimensions of the fan beam 41, or the cone beam 42, in a plane 14 perpendicular to the axis of rotation are chosen so that the examination zone 13 is completely irradiated, and the length of the rows of the detector arrangement is chosen to be such that the radiation beams 41 and 42 can be completely detected. The cone beam 42 is selected in conformity with the length of the detector columns in such a manner that the cone beam can be completely detected by the detector arrangement 16. In case only the fan beam 41 irradiates the examination zone, it is incident on the central detector row or rows.

When a technical object is concerned instead of a patient, the object can be rotated during an examination while the X-ray source 6 and the detector arrangement 15 remain stationary. The object can also be displaced parallel to the axis of rotation 14 by means of a motor. When the motors 5 and 2 run simultaneously, the radiation source S and the detector arrangement 16 perform a helical scanning motion.

Figure 2:
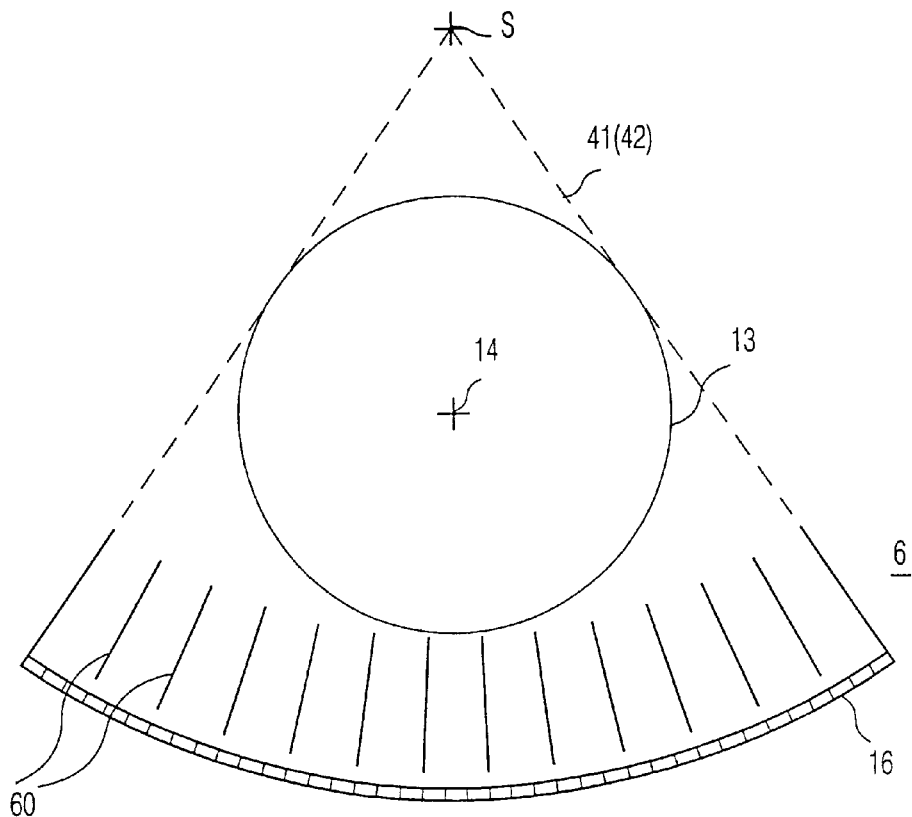
FIG. 2 is a sectional view of the arrangement shown in FIG. 1.

As is shown in FIG. 2, a collimator arrangement 6 which comprises a plurality of flat lamellas 60 is arranged between the examination zone 13 and the detector arrangement 16. The lamellas consist of a material that strongly absorbs the X-rays and are situated in planes which extend parallel to the axis of rotation 14 and intersect at the focus of the radiation source S. They may be spaced, for example 1 cm apart and each lamella may have a dimension of, for example, 20 cm in the plane of drawing. The collimator arrangement 6 thus subdivides the fan beam 41 into a number of neighboring segments so that essentially a column of detector elements can be struck only by primary radiation or scattered radiation from one segment.

The measuring data acquired by the detector arrangement 16 on the rotating gantry 1 is applied to an image processing computer 10 which is usually situated in a fixed location in space and is connected to the detector arrangement via a contactless data slip ring (not shown). The image processing computer 10 is capable of performing various image processing operations.

Figure 4:
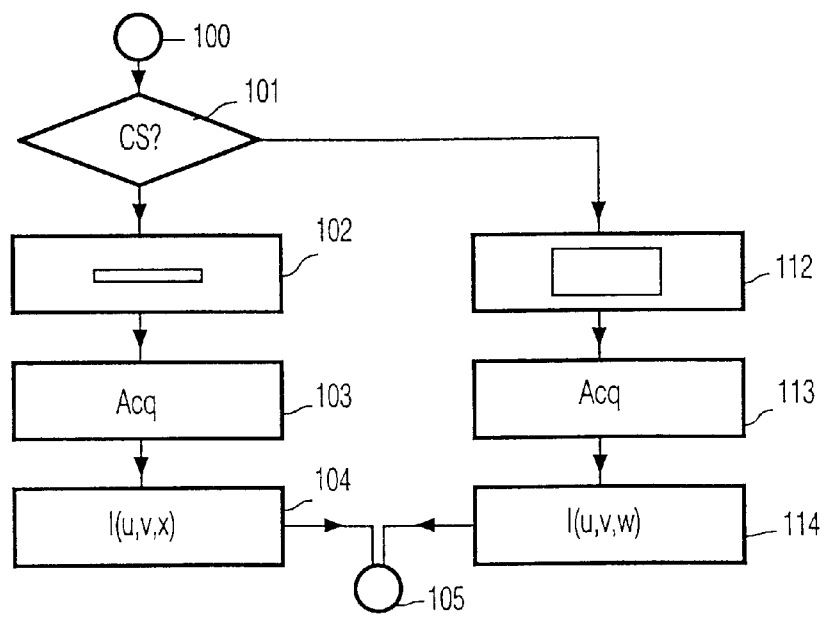
FIG. 4 shows a flow chart illustrating the various modes of operation.

The feasible modes of operation of the computed tomography apparatus shown will be described in detail hereinafter on the basis of the flow chart shown in FIG. 4.

After the initialization in the block 100, the mode of operation is selected in the step 101. When the first mode of operation (in which the scattered radiation is evaluated) is selected, the process proceeds to the step 102 in which the first diaphragm arrangement 31 on the one hand and the collimator arrangement 6 on the other hand are moved into the beam path. For the acquisition of the measuring values in the step 103, therefore, the fan beam 41 is generated. During the acquisition the gantry rotates so that the detector elements detect the primary radiation or the scattered radiation from a plurality of angular positions. The detector element or elements at the center of each detector column detects or detect the primary radiation whereas the scattered radiation (secondary radiation) is detected by the detector elements that are situated further outwards in a column.

Figure 3:
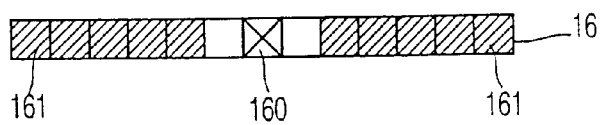
FIG. 3 is a plan view of a column of detector elements.

This is diagrammatically indicated in FIG. 3 which is a plan view of a column of detector elements. The detector elements 161, detecting the scattered radiation, are represented simply by shading whereas the detector element 160 (or the detector elements) at the center, detecting the primary radiation, is marked by a cross. Because of the finite dimensions of the focus of the radiation source, to both sides of said central detector element there are situated detector elements which are struck by scattered radiation but also by (reduced) primary radiation. It is useful not to take into account the signals from these detector elements (not shaded or denoted by a cross in the drawing) for the evaluation.

It is known that the momentum transfer X, whose spectrum is to be reconstructed as a function of the location u, v, is proportional to the product of the energy of the scattered X-ray quanta and the sine of half the scatter angle (the scatter angle is the angle enclosed by the trajectory of the scattered X-ray quantum relative to the trajectory that would have been followed by the X-ray quantum in the absence of scattering). On average the detector elements that are situated further outwards detect the scattered radiation at a scatter angle that is larger than that at which the detector elements situated further inwards detect the scattered radiation on average.

In order to enable determination of the momentum transfer, on the one hand the scatter angle and on the other hand the energy of the scattered X-ray quantum must be known. The scatter angle is given by the location of the detector element and the location of the point in the primary fan beam in which the scatter process has occurred. Either the energy of the scattered X-ray quanta must be measured, implying that the detector elements must be capable of measurement in an energy-resolved manner, or use must be made of X-rays with quantum energies from an as small as possible range (monochromatic X-rays in the ideal case). There are various possibilities for minimizing the energy difference $\Delta E$ of the X-ray quanta in relation to their energy E: The use of suitable filter materials (for example, copper) in the primary beam. The soft X-rays (being the X-rays of low quantum energy) produced by an X-ray source are thus suppressed to a high degree.

Additionally, the voltage in an X-ray tube can be optimized in respect of the choice of filter.

Finally, it is possible to apply the so-called "balanced filter" technique. The data is then acquired twice; filters having a respective slightly different atomic number are then arranged in the beam path and their K edge is used for filtering. Subsequently, the difference signal is extracted from the two measurements.

The location-dependent momentum transfer spectrum is reconstructed in the final step 104. Because the lamellas subdivide the fan beam into a number of segments which all have at least approximately the shape of a pencil beam, the reconstruction can be performed in conformity with the method disclosed in the cited D1. The execution of the method is thus completed (block 105).

However, if the second mode of operation is selected in the step 101, in which merely the attenuation of the primary radiation in the examination zone is reconstructed, the process proceeds to the block 112 in which the first diaphragm arrangement 31 is moved out of the beam path, so that only the second diaphragm arrangement 32 is still active and produces a cone beam 42. Moreover, in the block 112 the collimator 6 is removed from the area between the detector arrangement 16 and the examination zone 13.

During the subsequent acquisition of the measuring data the gantry rotates about the axis of rotation; all detector elements can then be struck by primary radiation (block 113). During the subsequent reconstruction step 114, the attenuation is reconstructed in a slice of the examination zone. A suitable reconstruction method is described in German patent application 198451334.

What is claimed is:

1. A computed tomography apparatus comprising:

a scanning unit which is rotatable relative to an examination zone, about an axis of rotation extending through the examination zone;

a radiation source which generates a radiation beam;

a diaphragm arrangement disposed between the radiation source and the examination zone in order to form a fan beam traversing the examination zone from the radiation beam;

a two-dimensional detector arrangement having a plurality of detector elements and a measuring surface, a part of which detects primary radiation from the fan beam whereas another part of the measuring surface detects scattered radiation produced in the examination zone; and a collimator arrangement interposed between the examination zone and the detector arrangement, the collimator arrangement including a plurality of lamellas disposed in planes that subdivide the fan beam into a number of segments so that the detector elements that are situated in a column extending parallel to the axis of rotation essentially are struck only by primary radiation or scattered radiation from one and the same segment.

2. A computed tomography apparatus as defined by claim 1, wherein the planes in which the lamellas are disposed intersect at the focus of the radiation source.

3. A computed tomography apparatus as defined by claim 1, wherein the computed tomography apparatus includes a first mode of operation in which a part of the detector elements detect the scattered radiation that is generated in the fan beam, and a second mode of operation in which the detector elements detect the primary radiation that is generated in a cone beam whose dimensions in the direction of the axis of rotation are larger than those of the fan beam.

4. A computed tomography apparatus as defined by claim 3, wherein in the first mode of operation a first diaphragm arrangement is disposed between the radiation source and the examination zone in order to generate the fan beam whereas in the second mode of operation a second diaphragm arrangement is active in the beam path in order to generate the cone beam.

5. A computed tomography apparatus as defined by claim 3, wherein the computed tomography apparatus utilizes a first computer program for calculating the scatter density distribution in the part of the examination zone traversed by the fan beam from the detector signals acquired in the first mode of operation, and a second computer program for calculating the attenuation of the primary radiation in the part of the examination zone traversed by the cone beam from the detector signals acquired in the second mode of operation.

6. A computed tomography apparatus comprising:

a scanning unit which is rotatable relative to an examination zone, about an axis of rotation extending through the examination zone;

a radiation source which generates a radiation beam;

a diaphragm arrangement disposed between the radiation source and the examination zone in order to form a fan beam traversing the examination zone from the radiation beam;

a two-dimensional detector arrangement having a plurality of detector elements and a measuring surface, a part of which detects primary radiation from the fan beam whereas another part of the measuring surface detects scattered radiation produced in the examination zone; and a collimator arrangement interposed between the examination zone and the detector arrangement, the collimator arrangement including a plurality of lamellas disposed in planes that subdivide the fan beam into a number of segments so that the detector elements that are situated in a column extending parallel to the axis of rotation essentially are struck only by primary radiation or scattered radiation from one and the same segment;

wherein the computed tomography apparatus utilizes a first computer program for calculating scatter density distribution in the part of the examination zone traversed by the fan beam, and a second computer program for calculating attenuation of primary radiation in the part of the examination zone traversed by a cone beam whose dimensions in the direction of the axis of rotation are larger than those of the fan beam.

* * * * *